(12) United States Patent  
Tan et al.

(10) Patent No.: US 7,349,085 B1
(45) Date of Patent: *Mar. 25, 2008

(54) DETECTING THE ORIENTATION OF CARBON NANOTUBES

(75) Inventors: Shida Tan, Milpitas, CA (US); Yuegang Zhang, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 591 days.

This patent is subject to a terminal disclaimer.

(21) Appl. No.: 10/797,234

(22) Filed: Mar. 10, 2004

(51) Int. Cl.
*G01J 9/00* (2006.01)
(52) U.S. Cl. .................... 356/364; 356/139.05
(58) Field of Classification Search ............... 356/364, 356/138, 139.05
See application file for complete search history.

(56) References Cited

U.S. PATENT DOCUMENTS

| 6,774,333 B2 * | 8/2004 | Hannah ................ 209/579 |
| 6,790,425 B1 * | 9/2004 | Smalley et al. ......... 423/447.1 |
| 2005/0147373 A1 * | 7/2005 | Zhang ................ 385/143 |

OTHER PUBLICATIONS

U.S. Appl. No. 10/746,078, filed Dec. 24, 2003, entitled "Controlling Carbon Nanotubes Using Optical Traps".
U.S. Appl. No. 10/669,150, filed Sep. 23, 2003, entitled "Sorting of Single-Walled Carbon Nanotubes Using Optical Dipole Traps".

* cited by examiner

*Primary Examiner*—Hwa (Andrew) Lee
(74) *Attorney, Agent, or Firm*—Trop, Pruner & Hu, P.C.

(57) ABSTRACT

Carbon nanotube orientation may be detected by exposing the carbon nanotube to a pair of laser beams oriented transversely to one another. By observing the effect on the intensity of transmitted light from a first laser beam when the polarization of the second laser beam is changed, the carbon nanotube orientation can be derived.

12 Claims, 3 Drawing Sheets

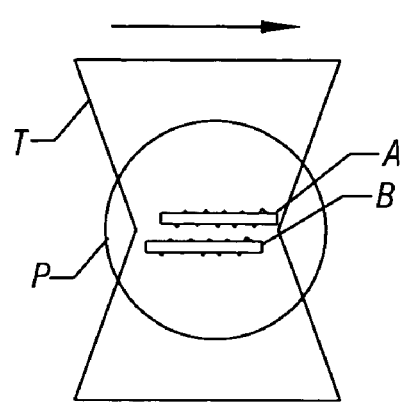
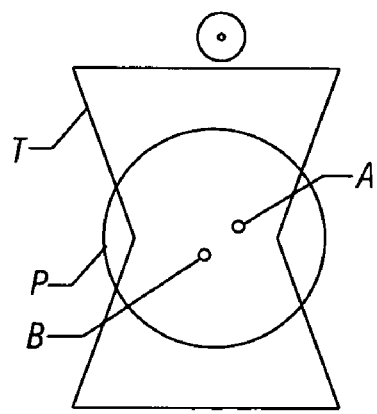
FIG. 2        FIG. 3
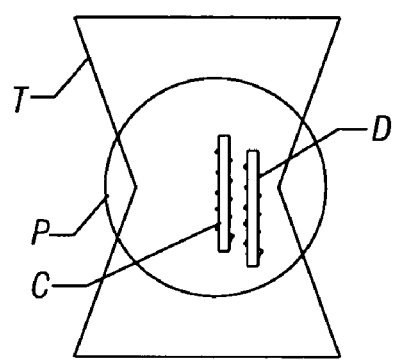
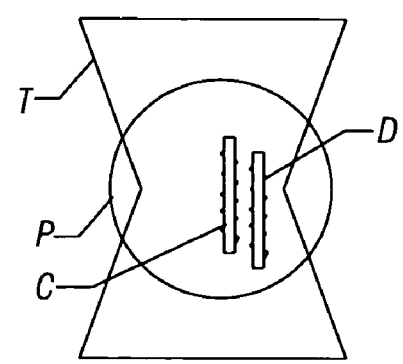
FIG. 4        FIG. 5
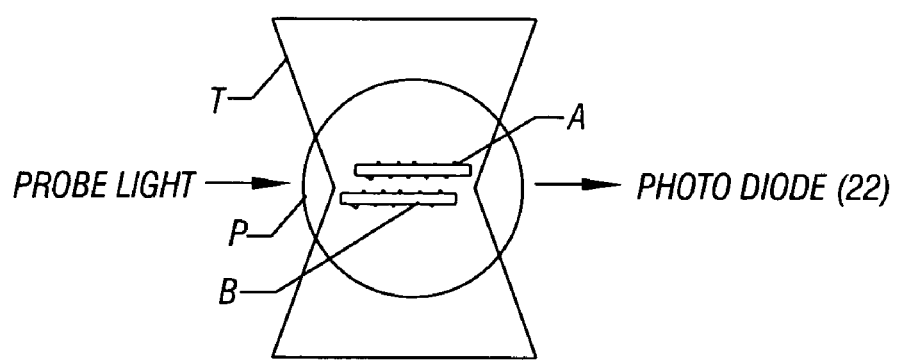
FIG. 6

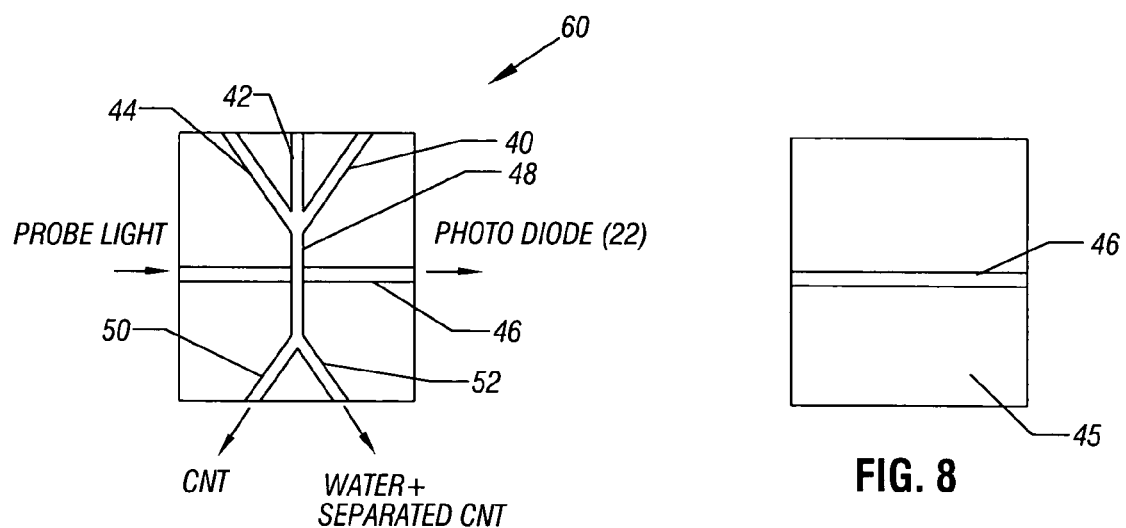
FIG. 7
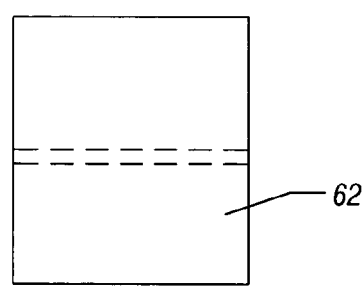
FIG. 9
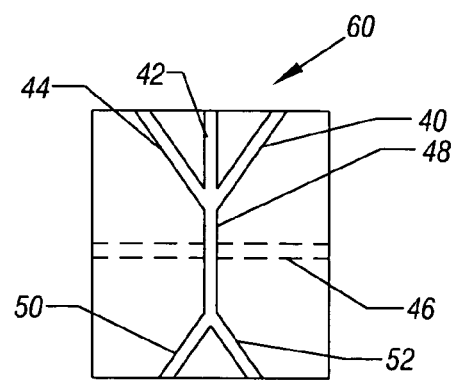
FIG. 8
FIG. 10
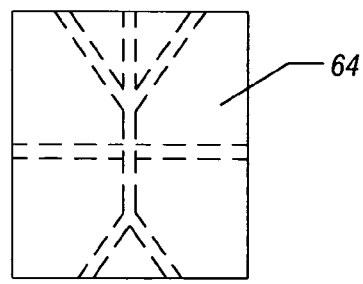
FIG. 11

DETECTING THE ORIENTATION OF CARBON NANOTUBES

BACKGROUND

This invention relates generally to the manipulation of carbon nanotubes.

Carbon nanotubes are known to have potential applications in a wide variety of areas. Potential applications include the fabrication of electronic devices, mechanical systems, and biological systems. Each of these applications generally comprehends the need to be able to manipulate individual carbon nanotubes. For example, in order to form a carbon nanotube-based field effect transistor, it would be desirable to align carbon nanotubes under a gate electrode with a gap between the carbon nanotubes. In a myriad of other examples, there is a need to manipulate carbon nanotubes.

Carbon nanotubes may be moved from one location to another. However, it would be desirable to know the orientations of the carbon nanotubes.

Single walled carbon nanotubes are extremely anisotropic, with diameters of about one nanometer and lengths of a few microns. While optical trapping and sorting of a single wall carbon nanotubes has been proposed, no existing theoretical model predicts the behavior and orientation of different species of carbon nanotubes in an optical trap. This is apparently due to the unique shape and optical properties of carbon nanotubes.

There are methods to observe carbon nanotubes, including transmission electron microscopy and scanning electron microscopy. However, these techniques cannot be used for determining the orientation of carbon nanotubes during manipulation.

Thus, there is a need for ways to control and detect the orientation of carbon nanotubes.

BRIEF DESCRIPTION OF THE DRAWINGS

FIG. 2 is a depiction of carbon nanotubes in an optical trap in one configuration in accordance with an embodiment of the present invention;

FIG. 3 is a depiction of carbon nanotubes in an optical trap in another configuration in accordance with one embodiment of the present invention;

FIG. 4 is a depiction of carbon nanotubes in an optical trap in one configuration in accordance with one embodiment of the present invention;

FIG. 5 is a depiction of carbon nanotubes in an optical trap in one configuration in accordance with one embodiment of the present invention;

FIG. 6 is a depiction of carbon nanotubes in an optical trap in accordance with one embodiment of the present invention;

FIG. 7 is a top plan view of a microfluidic chip and corresponds to the side view shown in FIG. 6 in accordance with one embodiment of the present invention;

FIG. 8 is a top plan view of the fabrication of the chip shown in FIG. 7 at an early stage of manufacture in accordance with one embodiment of the present invention;

FIG. 9 is a top plan view corresponding to FIG. 8 at a later stage of manufacture in accordance with one embodiment of the present invention;

FIG. 10 is a top plan view corresponding to FIG. 9 at a later stage of fabrication in accordance with one embodiment of the present invention; and FIG. 11 is a top plan view corresponding to FIG. 10 at a subsequent stage of manufacture in accordance with one embodiment of the present invention.

DETAILED DESCRIPTION

Figure 1:
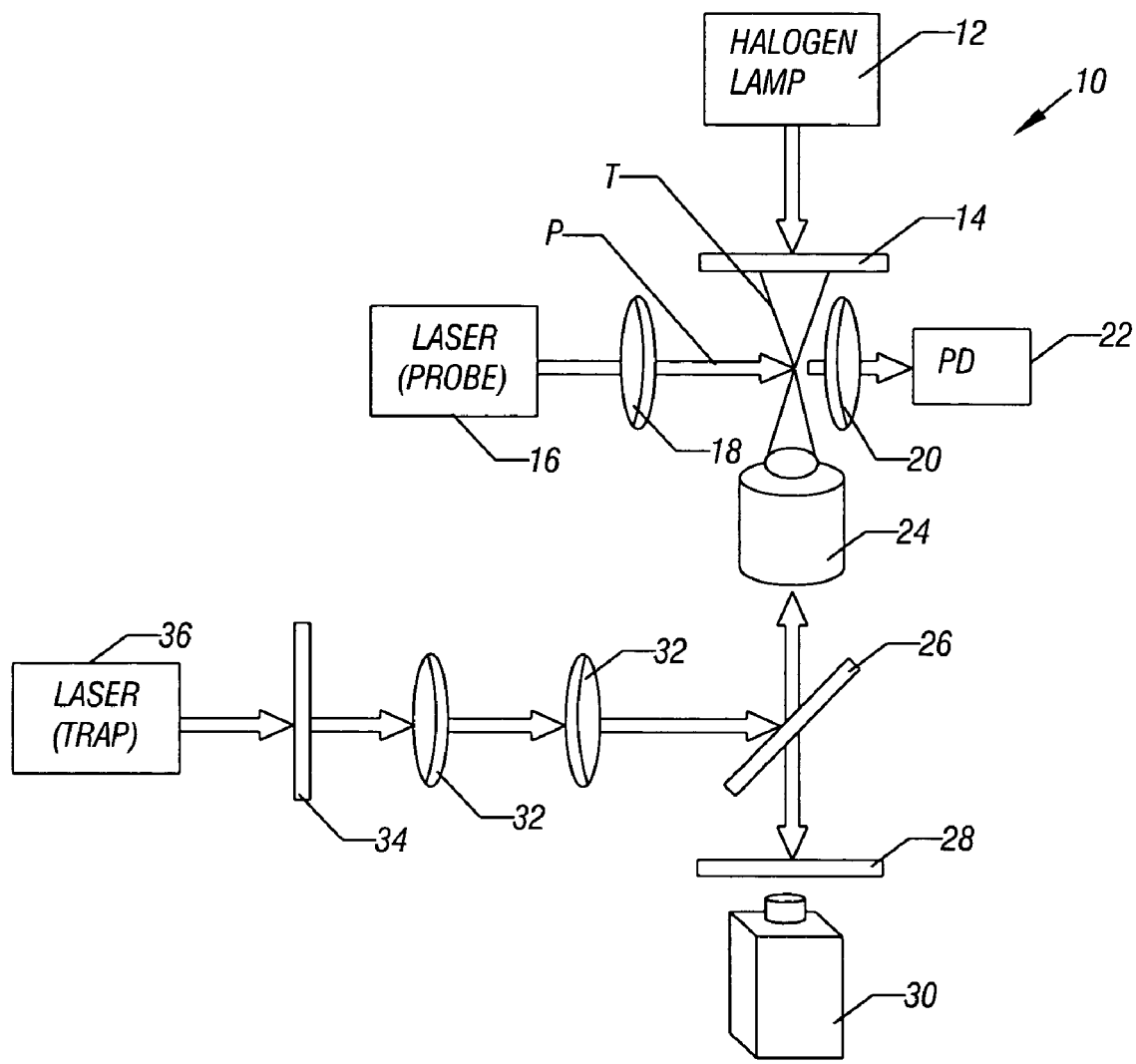
FIG. 1 is a schematic depiction of a system useful in accordance with one embodiment of the present invention.

Referring to FIG. 1, an apparatus 10 for detecting the orientation of carbon nanotubes includes a probe laser 16, including optics 18. The probe laser light P is detected by a photodetector 22 which receives the light through optics 20.

A halogen lamp 12 acts as the imaging illumination light source. A polarizer 14 provides the desired polarization to the illumination light. Light from the lamp 12 passes downwardly through the dichroic mirror 26 to be received by an analyzer 28 and imaged by a camera 30 in one embodiment.

The trap laser light is generated by the laser 36. The polarization of the laser light is controlled by a quarter wave plate 34. That light passes through quarter wave plate 34 and a plurality of telescopic lenses 32. One component of the light from the trap laser 36 may be reflected by a dichroic mirror 26 and passes through a microscope objective lens 24 to provide the optical trap T.

A focused laser beam can trap a carbon nanotube through the interaction between the electric field of the laser beam and the spontaneous dipole momentum induced in the nanotube. The induced dipole momentum of a neutral particle in the electric field of a laser beam can be expressed as:

$$P = \epsilon_0 \chi E \quad (1)$$

where P is the polarization or dipole momentum per unit volume, $\epsilon_0$ is the permittivity of free space, $\chi$ is the dielectric susceptibility, and E is the electric field.

The potential energy may be expressed as:

$$U = (-\tfrac{1}{2})\langle P \cdot E \rangle = (-\tfrac{1}{2})\epsilon_0 \chi \langle E \rangle^2 \quad (2)$$

The dielectric susceptibility may be expressed in a complex form as a function of frequency as follows:

$$\chi(\omega) = \chi'(\omega) + i\chi''(\omega) \quad (3)$$

where $\chi'(\omega)$ is the real part and $\chi''(\omega)$ is the imaginary part. When $\omega < \omega_0$, $\chi'(\omega) > 0$, where $\omega_0$ is a resonant frequency.

From equation (2), the potential energy U decreases when the light intensity increases. Furthermore, the nanotube tends to move to an area of higher E so it becomes trapped at the center of the trap laser beam, assuming that the optical intensity distribution of the laser beam is Gaussian.

Depending on the diameter and chirality, a single walled carbon nanotube may be metallic or semiconductor. The electron density of states of a nanotube is composed of many spikes, called the van Hove singularities. The energy gaps between the corresponding van Hove singularities are optically allowed inter-band transition energies. By choosing a proper laser frequency or continuously tuning the laser frequency, a certain type of nanotube can be trapped.

A multiple walled carbon nanotube is an assembly of multiple single walled nanotubes with different diameters and chiralities. The trapping of a multiple walled carbon nanotube depends on its composition, i.e., the ratio of different single walled nanotube types. A laser frequency that can trap all types of single walled nanotubes can also trap multiple walled carbon nanotubes.

The nanotubes can also be aligned using a polarized laser beam. The dipole is parallel to the axis of the nanotube. The polarization P may be decomposed into a parallel component $P_p$ and an orthogonal component $P_o$:

$$P = P_p + P_o \approx P_p = \epsilon_0 \chi E_p \quad (4)$$

where $E_p$ is the parallel component of E.

The potential energy can then be expressed as:

$$U = (-1/2)\langle P \cdot E \rangle = (-1/2)\langle E_p \rangle^2 \cos\theta \quad (5)$$

where θ is the angle between E and the axis of a carbon nanotube.

From the above equations, an increase in E leads to a decrease in U. Also, a decrease in θ leads to a decrease in U when $\omega < \omega_0$, $\chi'(\omega) > 0$. Therefore, carbon nanotubes can be trapped and aligned by polarized laser beam from the laser 36.

A single walled carbon nanotube may be modeled as a strip of graphite sheet rolled up into a seamless cylinder with a diameter in the nanometer scale. Due to quantum confinement in the circumferential direction, nanotubes have unique electronic structure and optical properties that are different from those of graphite. The absorption (and/or scattering) coefficient of single walled carbon nanotubes is much higher when the polarization of the light is parallel to the nanotube axis.

An optical scattering force pushes the carbon nanotubes and tends to align the carbon nanotube axis with the optical beam axis. Conversely, an induced dipole in the carbon nanotubes along the tube axis tends to align with polarization of the trap laser light. Therefore, the tube axis orients perpendicularly to the optical axis of the trap laser 36. The two competing forces exerted on carbon nanotubes in an optical trap T depend on the properties of these carbon nanotubes. In some carbon nanotubes the optical scattering force dominates, and in other carbon nanotubes the effect of the induced dipole dominates.

By using the probe laser 16 light P propagating in a direction transverse to that of the optical trap laser beam and monitoring the transmitted light intensity in the detector 22 as the polarization direction of the optical trap laser beam is changed, the dominant force in the optical trap T for the carbon nanotubes in the trap can be detected.

Where the scattering force is dominant in the carbon nanotube, the carbon nanotube axis aligns with the optical axis of the laser trap beam. Therefore, the variation in polarization direction of the trap laser beam does not effect the transmission of the light from the probe laser 16.

Conversely, if the alignment of the induced dipole with the optical trap laser polarization is a dominant effect for a given carbon nanotube, the transmitted intensity varies periodically with periodic change of polarization direction of the optical trap laser beam.

Therefore, by monitoring the intensity in the photodetector 22 of the change of the transmitted probe beam P, the orientation of the carbon nanotubes in an optical trap T can be derived.

FIG. 2 shows the optical trap T (propagating upwardly) and probe laser beam P (propagating into the page) also shown in FIG. 1. A pair of carbon nanotubes A and B are illuminated by both beams. The direction of trap laser beam polarization is indicated by the arrow over FIG. 2. In FIG. 3, the polarization of the trap laser beam has been rotated 90 degrees as indicated by the symbol over the figure.

The carbon nanotubes A and B rotate from FIG. 2 to FIG. 3 to align with the laser beam polarization since they are now extending into the page in FIG. 3. This may be detected by the probe laser beam P and the detector 22 which sees different intensities, depending on whether the carbon nanotubes are arranged across the probe beam P, as indicated in FIG. 2, or aligned with it, as indicated in FIG. 3.

Thus, by monitoring the intensity of the light received by the photodetector 22, generated by the probe laser beam P, and changing the polarization of the optical trap laser 36, one can determine whether the carbon nanotubes respond to polarization changes of trap laser T.

For example, as shown in FIGS. 4 and 5, the carbon nanotubes C and D do not align in response to the changes of trap laser beam polarization (as indicated above FIGS. 2 and 3). In FIGS. 4 and 5, despite the change in laser beam polarization from the trap laser 36, the carbon nanotubes C and D do not reorient.

If the transmitted probe light intensity remains unchanged with various optical trap laser beam polarization directions, as suggested in FIGS. 4 and 5, the optically trapped carbon nanotubes have an orientation with their tube axes mostly aligned with the trap laser beam axis. If the transmitted probe light intensity changes periodically, as the change in optical trap laser beam polarization changes, as is in the case of FIGS. 2 and 3, the optically trapped carbon nanotubes have orientations with the tube axis mostly perpendicular to the trap laser beam optical axis.

When the carbon nanotubes are aligned with the optical axis, as shown in FIGS. 4 and 5, even if the carbon nanotubes rotate about their tube axes due to the change of the trap laser beam polarization direction, the transmission of the probe laser beam will not be changed. When the carbon nanotubes are perpendicular to the optical axis of the trapping beam T, as is the case in FIGS. 2 and 3, the attenuation of the second laser beam is dependent on the orientation of the trapping beam polarization. Thus, by monitoring the transmitted probe light intensity, the orientation of the carbon nanotubes in the optical trap T can be derived.

In the open optical detection system 10, probe laser P can be replaced by any other type of light source. The propagation direction of probe light P and the photodetector may also be aligned with the optical axis of trap laser T if a proper filter is used. For example, detection of transmission change of the light from the light source 12 by changing the polarization of trap laser T could also provide the orientation information. Furthermore, by changing the polarization of light source 12 using polarizer 14, it is possible to detect the in-plane orientation of nanotubes that are perpendicular to the trap laser T.

Once the change in transmission is detected, the dependency of the carbon nanotube orientation on trapped laser wavelength and intensity can also be studied. This study may aid in optimizing the optical trapping and sorting of single walled carbon nanotubes.

An integrated detection device is illustrated in FIGS. 6 and 7. In FIG. 6, the trapping beam T is illustrated and the probe beam P is illustrated. The probe light direction is indicated, as is the orientation of the photodiode 22. It corresponds to what has already been described with respect to FIGS. 2-5.

However, as shown in FIG. 7, looking down from above, it is seen that the microfluidic chip 60 includes a series of channels 40, 42, and 44 that communicate with a throat 48 that in turn communicates with output channels 50 and 52. A waveguide 46 conducts probe light P transversely to the throat 48 to the photodiode 22. In this case, the trap beam T is extending upwardly from below the page, transverse to the plane of the page of FIG. 7.

Carbon nanotubes may be introduced in the channel 44 and water may be introduced in the channels 42 and 40. Certain carbon nanotubes may be separated to the channel 50 and other carbon nanotubes may be separated to the channel 52. Separation may be achieved by steering the carbon nanotubes based on characteristics such as detected orientation or other characteristics using the trapping laser beam T. In some embodiments, a different flow may be provided at different levels within the throat 48. Thus, the carbon nanotubes may be manipulated into different flows to cause them to separate, depending on detected characteristics.

The microfluidic chip 60 may be formed by forming a waveguide 46 in a substrate 45 as shown in FIG. 8. The substrate 45 may be formed of a variety of materials including glass, quartz, or silicon. The waveguide 46 may be defined by photolithographic methods, followed by doping of a selected area.

A silicon substrate 45, in one embodiment, may have a relatively thick silicon dioxide layer 62 overlying it as shown in FIG. 9. For example, a silicon dioxide layer 62 of 10 microns may be utilized. The silicon dioxide layer 62, in one embodiment, may form the bottom cladding for the substrate 45. The core of the waveguide 46 can be defined through a photolithography process followed by doping. Another silicon dioxide layer (e.g., 10 microns thick) may be deposited on top of the waveguide 46 to form the top cladding for the waveguide device.

The microfluidic channels 40, 42, 44, the throat 48, and the channels 50 and 52 are etched in the substrate 45 with the main channel oriented perpendicular to that of the optical waveguide channel, as shown in FIG. 10. Now the integrated optical waveguide device may be formed within a microfluidic chip 60 by joining the substrate 45 and a polydimethylsiloxane (PDMS) elastomer layer 64, treated by oxygen plasma, and then bonded together, as indicated in FIG. 11, with the PDMS layer 64 on top.

An integrated optical waveguide device may also be formed within the microfluidic chip 60. Lasers and photodiodes may be coupled to the waveguide 46 to detect the trapped laser polarization effect on the carbon nanotube orientation. The coupling of the devices to the waveguide 46 may be fiber coupling or through free space, to mention two examples.

Alternatively, further integration may be achieved by integrating both the laser and the photodiode onto the chip 60. One advantage of such a device is that the measurement uncertainty of the light intensity may be reduced since the waveguides are pre-aligned by such an arrangement.

In some embodiments, sorting of carbon nanotubes and monitoring may occur in one step. By measuring the transmission spectrum and analyzing the orientation variation of the carbon nanotubes in an optical trap, the dependency of the optical trapping process on trap laser wavelength and intensity can also be derived.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:
   illuminating a carbon nanotube with a first laser beam and a second laser beam transverse to one another; and
   monitoring the effect on transmission of light from said first laser beam as the polarization of the second laser beam is changed.

2. The method of claim 1 wherein monitoring the effect on transmission of light includes monitoring the intensity of light transmitted.

3. The method of claim 1 including passing a carbon nanotube through a microfluidic chip.

4. The method of claim 3 including passing said carbon nanotube through a passage through said chip.

5. The method of claim 4 including providing a waveguide through said chip transverse to said passage and illuminating said waveguide with said first laser beam.

6. The method of claim 1 including trapping a carbon nanotube using said second laser beam.

7. The method of claim 6 including moving said carbon nanotube using said second laser beam.

8. The method of claim 1 including determining whether the carbon nanotube reorients in response to a change in polarization of said second laser beam.

9. An apparatus comprising:
   a first laser;
   a second laser;
   an optical trap wherein said first laser and second laser extend transversely to one another;
   a device to change the polarization of said second laser; and
   a detector to detect the effect on light from said first laser when the polarization of said second laser is changed.

10. The apparatus of claim 9 wherein said device is a diffractive lens.

11. The apparatus of claim 9 wherein said detector is a photodetector to detect the intensity of transmitted laser light from said first laser.

12. The apparatus of claim 9 including a mirror to reflect light from said second laser into an optical trap in a direction transverse to the direction of propagation of light from said first laser.

* * * * *